(12) United States Patent
Courtney et al.

(10) Patent No.: US 7,326,727 B2
(45) Date of Patent: Feb. 5, 2008

(54) FURANTHIAZOLE DERIVATIVES AS HEPARANASE INHIBITORS

(75) Inventors: Stephen Martin Courtney, Abingdon (GB); Philip Andrew Hay, Abingdon (GB); David Ian Carter Scopes, Abingdon (GB)

(73) Assignee: Oxford Glycosciences (UK) Ltd., Oxfordshire (GB)

( * ) Notice: Subject to any disclaimer, the term of this patent is extended or adjusted under 35 U.S.C. 154(b) by 0 days.

(21) Appl. No.: 10/523,118

(22) PCT Filed: Aug. 5, 2003

(86) PCT No.: PCT/GB03/03409

§ 371 (c)(1),
(2), (4) Date: Oct. 4, 2005

(87) PCT Pub. No.: WO2004/013132

PCT Pub. Date: Feb. 12, 2004

(65) Prior Publication Data

US 2006/0128768 A1  Jun. 15, 2006

(30) Foreign Application Priority Data

Aug. 5, 2002 (GB) ................................ 0218147.7

(51) Int. Cl.
*A61K 31/427* (2006.01)
(52) U.S. Cl. .................................................. 514/365
(58) Field of Classification Search ................. 514/365
See application file for complete search history.

(56) References Cited

FOREIGN PATENT DOCUMENTS

| DE | 199 55 803 | 5/2001 |
| GB | 0 218 147 | 7/1924 |
| WO | WO 01/35967 A1 | 5/2001 |
| WO | WO 2004/013132 A1 | 2/2004 |

OTHER PUBLICATIONS

Oleinik et al., CA 78:43169, 1973.*
Golub et al., Science, vol. 286, Oct. 15, 1999, pp. 531-537.*
Bashkin, P., et al., "Basic fibroblast growth factor binds to subendothelial extracellular matrix and is released by heparitinase and heparin-like molecules," *Biochemistry*, 1989, 28, 1737-1743.
CAS Registry No. 338786-69-9, XP-002259645, 2003, 1 page.

Demir, M., et al., "Anticoagulant and antiprotease profiles of a novel natural heparinomimetic mannopentaose phosphate sulfate (PI-88)," *Clin. Appl. Thromb. Hemost.*, 2001, 7(2), 131-140.
Folkman, J., et al., "control of angiogenesis by heparin and other sulfated polysaccharides," *Adv. Exp. Med. Biol.*, 1992, 313, 355-364.
Hollenberg, D.H., et al., "Nucleosides. 102. Synthesis of some 3'-deoxy-3'-substituted arabinofuranosylpyrimiding nucleosides," *J. Med. Chem.*, 1977, 20(1), 113-116, Accession No. 833809, 1 page.
Kempter, G., et al., "Mehrfach heterocyclish substutuierte thiazole," *Z. Chem.*, 1970, 10(12), 460-462 (German, no English abstract available).
Parish, C.R., et al., "identification of sulfated oligosaccharide-based inhibitors of tumor growth and metastasis using novel in vitro assays for angiogenesis and heparanase activity," *Cancer Res.*, 1999, 59, 3433-3441.
Sarodnick, G., et al., "Heterocyclic substituted thiazoles as thiabendazole analogues," *Z. Chem.*, 1979, 19(1), 21-22 (German, no English abstract available).
Tyle, P., "Iontophoretic devices for drug delivery," *Pharmaceutical Research*, 3(6), 1986, 318-326.
Vlodavsky, I, et al., "Expression of heparanase by platelets and circulating cells of the immune system: possible involvement in diapedesis and extravasation," *Invasion Metastasis*, 1992, 12, 112-127.
Vlodavsky, I., et al., "Inhibition of tumor metastasis by heparanase inhibiting species of heparin," *Invasion Metastasis*, 1994, 95, 290-302.
Vlodavsky, I., et al., "Mammalian heparanase: gene cloning, expression and function in tumor progression and metastasis," *Nature Medicine*, 1999, 5(7), 793-802.

* cited by examiner

*Primary Examiner*—Laura L. Stockton
(74) *Attorney, Agent, or Firm*—McDonnell Boehnen Hulbert & Berghoff LLP

(57) ABSTRACT

The invention provides a compound of formula (I) or a pharmaceutically acceptable salt or prodrug thereof: (I) wherein the groups Q, $R^2$, $R^3$, $R^4$ and $R^5$ represent various substituent groups, and their use as inhibitors of heparanase.

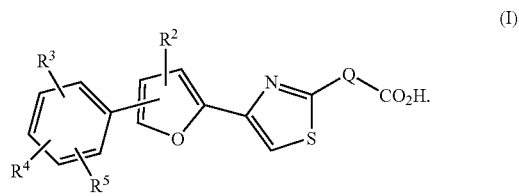

(I)

1 Claim, No Drawings

FURANTHIAZOLE DERIVATIVES AS HEPARANASE INHIBITORS

The present invention relates to novel furanthiazole derivatives which are useful as inhibitors of heparanase, methods for their synthesis, pharmaceutical compositions comprising them and their use in medicine, in particular for the treatment of cancer.

The extracellular matrix (ECM) is not only the structural surround for cells in a multicellular organism but also acts as a key modulator and mediator of their physiology, differentiation, organisation and repair. Receptor ligands are stored, concentrated, processed and presented to the cell surface by components of the ECM, which include free and protein-bound heparan sulfate proteoglycans, free and protein-bound chondroitins, collagens, a variety of cell-adhesive integrins such as fibronectin. The ECM is also in a constant flux of degradation and synthesis by neighbouring cells.

The ECM is the principal barrier to tumour growth and metastasis. For a tumour cell to penetrate this barrier it must sufficiently degrade the ECM components so that there is ample space to traverse. The ECM must also be degraded in order to provide avenues for new blood vessel formation in order to supply the increased nutrient requirements of rapidly growing tumours (angiogenesis).

A broad spectrum of degradative enzymes are secreted by tumor cells to break down the ECM's complex composition. However, recent studies have demonstrated that inhibiting even just one ECM degrading enzyme appears to provide significant benefit in treating cancer. For example, inhibitors of certain proteases that degrade ECM protein component have been studied in preclinical and clinical trials as anti-cancer agents.

Carbohydrates represent a large fraction of the total mass of all ECM. Therefore, tumour cells secrete large quantities of carbohydrate degrading enzymes as they penetrate the ECM. In fact, there is good correlation between raised levels of carbohydrate processing enzymes, such as heparanases, secreted by tumour cells and their metastatic potential (e.g. Vlodavsky et al., (1994) *Invasion Metastasis* 14:290-302; (1999) *Nature Medicine* 5:793-802). Heparanases are enzymes that can degrade heparan sulfate as well as heparin and heparan sulfate proteoglycans.

The carbohydrate fragments generated by glycosidase action also promote the cancer phenotype since many are growth-stimulatory. For example, heparanase activity can release heparan sulfate fragments which can increase the potency of a variety of growth factors and heparan sulfate fragments can elicit cell growth stimulation when they are bound by the appropriate cell surface receptors (e.g. Folkman and Shing (1992) *Adv. Exp. Med. Biol.* 313:355-64).

Inhibitors of ECM carbohydrate degradation are potent anticancer agents. For example, sulfated oligosaccharide heparanase inhibitors block tumour metastasis in some animal models (Vlodavsky et al., (1994) *Invasion Metastasis* 14:290-302; Parish et al., (1999) *Cancer Res.* 59:3433-41). Furthermore, heparanase activity results in the release of growth factors that can stimulate angiogenesis and promote tumour growth (Bashkin et al., (1989) *Biochemistry* 28: 1737-43).

Heparanase activity correlates with the ability of activated cells of the immune system to leave the circulation and elicit both inflammatory and autoimmune responses. Interaction of platelets, granulocytes, T and B lymphocytes, macrophage and mast cells with the subendothelial ECM is associated with degradation of heparan sulfate by heparanase activity (Vlodavsky et al., (1992) *Invasion Metastasis*, 12, 112-127). Heparanase inhibitors may be able to prevent or inhibit the progression of autoimmune and inflammatory diseases.

Heparinomimetic compounds are currently being developed as anticoagulant and antiproliferative agents for the control of thrombotic and proliferative disorders (Demir et al., *Clin. Appl. Thromb. Hemost.* 2001 April; 7(2): 131-40). Thus, a secondary function of heparanase inhibitors may have a role in cardiovascular diseases including blood-clotting conditions, for example thromboembolic disease, arterial thrombosis and restenosis.

WO01/35967 discloses the use of heparanase inhibitors for the treatment or prevention of congestive heart failure e.g. primary cardiomyopathy. Associated conditions treated or prevented with the inhibitor include peripheral oedemas, pulmonary and hepatic congestion, dyspnoea, hydrothorax and ascites. Renal problems, e.g. nocturia can also be treated.

CAS Registry No. 338786-69-9 discloses the compound 2-[4-[5-(2,4-dichlorophenyl)furan-2-yl]-1,3-thiazol-2-yl] acetic acid, no pharmaceutical utility is suggested for this compound.

The present invention provides a class of compounds, which can be used as inhibitors of heparanase. These compounds provide the opportunity for establishing new treatments for cancer, angiogenesis, inflammatory and autoimmune conditions and cardiovascular diseases.

The invention provides a compound of formula (I) or a pharmaceutically acceptable salt or prodrug thereof:

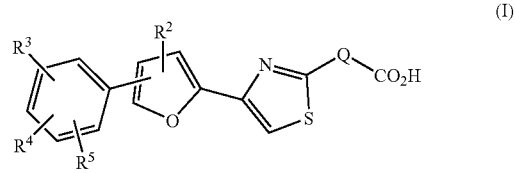

(I)

wherein

Q is $(CH_2)_m[CH(R^1)]_n(CH_2)_p$ where n is 0 or 1, and m and p are independently 0, 1 or 2;

$R^1$ is hydrogen, $C_{1-6}$ alkyl, $C_{2-6}$ alkenyl or $C_{3-6}$ alkynyl;

$R^2$ is hydrogen, halogen, $C_{1-6}$ alkyl optionally substituted by hydroxy or $C_{1-6}$ alkoxy, or phenyl optionally substituted by one or more substituents selected from halogen, $C_{1-6}$ alkyl, $CF_3$, $OCF_3$, $OR^6$, CN and methylenedioxo;

$R^3$, $R^4$ and $R^5$ are independently hydrogen, halogen, $C_{1-6}$ alkyl optionally substituted by hydroxy or $C_{1-6}$ alkoxy, $CF_3$, $OR^6$, $COR^7$, $NHCOR^8$, $NHCONHR^8$, $NHSO_2R^8$, $CONHR^9$, CN, $SO_2R^8$ or $NR^{10}R^{11}$;

$R^6$ is hydrogen, $C_{2-6}$ alkenyl, $C_{3-6}$ alkynyl, $C_{1-6}$ alkyl optionally substituted by hydroxy or $C_{1-6}$ alkoxy, aryl or heteroaryl wherein aryl or heteroaryl is optionally substituted by one or more substituents selected from halogen, $CF_3$, $OCF_3$, CN, $C_{1-6}$ alkyl, $C_{1-6}$ alkoxy and methylenedioxo;

$R^7$ is $C_{1-6}$ alkyl, $OR^6$ or phenyl optionally substituted by one or more substituents selected from halogen, $CF_3$, $OCF_3$, CN, $C_{1-6}$ alkyl, $C_{1-6}$ alkoxy and $NHCOR^8$;

$R^8$ is $C_{1-6}$ alkyl, $C_{2-6}$ alkenyl or $C_{1-6}$ alkoxy any of which may be optionally substituted by aryl or heteroaryl, wherein the aryl or heteroaryl is optionally substituted by one or more substituents selected from halogen, $CF_3$, $OCF_3$, $OR^6$, CN, $C_{1-6}$ alkyl, methylenedioxo and $NR^{10}R^{11}$; $C_{3-6}$ cycloalkyl wherein the ring may contain up to two heteroatoms selected from $NR^{12}$, S and O; or aryl or heteroaryl wherein the aryl or heteroaryl is optionally substituted by one or more substituents selected from halogen, $CF_3$, $OCF_3$, $OR^6$, CN, $C_{1-6}$ alkyl, methylenedioxo and $NR^{10}R^{11}$;

$R^9$ is $C_{1-6}$ alkyl, $C_{1-6}$ alkylphenyl or phenyl, wherein alkyl may be interrupted by oxygen and wherein phenyl is optionally substituted by one or more substituents selected from halogen, $C_{1-6}$ alkyl, $CF_3$, $OCF_3$, CN, $C_{1-6}$ alkoxy and methylenedioxo;

$R^{10}$ and $R^{11}$ are independently hydrogen or $C_{1-6}$ alkyl, or together with the nitrogen to which they are attached form a 5- to 6-membered heterocyclic group which optionally contains an additional heteroatom selected from $NR^{12}$, O and S; and $R^{12}$ is hydrogen or $C_{1-6}$ alkyl;

provided that the compound is not:

i) 2-[4-[5-(2,4-dichlorophenyl)furan-2-yl]-1,3-thiazol-2-yl]acetic acid.

In the compounds of formula (I):

The $R^3$, $R^4$ and $R^5$ substituted phenyl group is preferably on the 5-position of the furan ring.

n is preferably 0.

Q is preferably $CH_2$.

$R^2$ is preferably hydrogen or halogen. More preferably $R^2$ is hydrogen.

Preferably at least one of $R^3$, $R^4$ and $R^5$ is other than hydrogen.

$R^3$, $R^4$ and $R^5$ are preferably independently, hydrogen, halogen, $C_{1-6}$ alkyl optionally substituted by hydroxy or $C_{1-6}$ alkoxy, $CF_3$, $OR^6$, $NHCOR^8$ or $CONHR^9$. More preferably $R^3$ and $R^4$ are independently, hydrogen, halogen or $NHCOR^8$ and $R^5$ is hydrogen. Even more preferably one of $R^3$ and $R^4$ is $NHCOR^8$ and the other is hydrogen or halogen. When one of $R^3$, $R^4$ and $R^5$ is $NHCOR^8$ this group is preferably on the 4-position of the phenyl ring.

$R^6$ is preferably hydrogen, $C_{2-6}$ alkenyl, $C_{3-6}$ alkynyl, $C_{1-6}$ alkyl optionally substituted by hydroxy or $C_{1-6}$ alkoxy, or phenyl optionally substituted by one or more substituents selected from halogen, $CF_3$, $OCF_3$, CN, $C_{1-6}$ alkyl, $C_{1-6}$ alkoxy and methylenedioxo. More preferably $R^6$ is hydrogen or $C_{1-6}$ alkyl, e.g. $C_{1-6}$ alkoxy.

$R^7$ is preferably hydroxy or $C_{1-6}$ alkoxy.

$R^8$ is preferably $C_{1-6}$ alkyl, $C_{2-6}$ alkenyl or $C_{1-6}$ alkoxy any of which may be optionally substituted by phenyl wherein the phenyl is optionally substituted by one or more substituents selected from halogen, $CF_3$, $OCF_3$, $OR^6$, CN, $C_{1-6}$ alkyl, methylenedioxo and $NR^{10}R^{11}$; $C_{3-6}$ cycloakyl wherein the ring may contain up to two heteroatoms selected from $NR^{12}$, S and O; phenyl optionally substituted by one or more substituents selected from halogen, $C_{1-6}$ alkyl, $C_{1-6}$ alkoxy, $CF_3$, $OCF_3$, $OR^6$, CN and methylenedioxo; or a 5- to 10-membered mono- or bicyclic heteroaryl group containing up to three heteroatoms selected from O, N and S which heteroaryl group may be substituted by $C_{1-6}$ alkyl, $C_{1-6}$ alkoxy or halogen. More preferably $R^8$ is $C_{1-6}$ alkyl, $C_{2-6}$ alkenyl or $C_{1-6}$ alkoxy any of which may be optionally substituted by phenyl wherein the phenyl is optionally substituted by one or more substituents selected from halogen, $CF_3$, $OCF_3$, $OR^6$, CN, $C_{1-6}$ alkyl, methylenedioxo and $NR^{10}R^{11}$; phenyl optionally substituted by one or more substituents selected from halogen, $CF_3$, $OCF_3$, $OR^6$, CN, $C_{1-6}$ alkyl, methylenedioxo and $NR^{10}R^{11}$; phenyl optionally substituted by one or more substituents selected from halogen, $C_{1-6}$ alkyl, $CF_3$, $OCF_3$, $OR^6$, CN and methylenedioxo; or a 5- to 10-membered mono- or bicyclic heteroaryl group containing up to three heteroatoms selected from O, N and S which heteroaryl group may be substituted by $C_{1-6}$ alkyl, $C_{1-6}$ alkoxy or halogen. In particular $R^8$ is $C_{1-6}$ alkyl or $C_{2-6}$ alkenyl either of which may be optionally substituted by phenyl wherein the phenyl is optionally substituted by one or more substituents selected from halogen, $C_{1-6}$ alkyl, $CF_3$, $OCF_3$, $OR^6$, CN, methylenedioxo and $NR^{10}R^{11}$; or phenyl optionally substituted by one or more substituents selected from halogen, $C_{1-6}$ alkyl, $CF_3$, $OCF_3$, $OR^6$, CN methylenedioxo and $NR^{10}R^{11}$.

A specific group of compounds that may be mentioned are those compounds where $R^8$ is phenyl optionally substituted by one or more substituents selected from halogen, $C_{1-6}$ alkyl, $C_{1-6}$ alkoxy, $CF_3$, $OCF_3$, $OR^6$, CN and methylenedioxo.

When $R^8$ is $C_{2-6}$ alkenyl optionally substituted by aryl or heteroaryl, e.g. phenyl, it is preferably a $C_2$ alkenyl group.

In the group $NR^{10}R^{11}$, when the $R^{10}$ and $R^{11}$ substituents, together with the nitrogen to which they are attached form a 5- or 6-membered ring, the ring may be, for example, morpholine, piperazine or N-methylpiperazine.

The term "alkyl" as used herein whether on its own or as part of a larger group e.g. "alkoxy" includes both straight and branched chain radicals. The term alkyl also includes those radicals wherein one or more hydrogen atoms are replaced by fluorine.

The term "alkenyl" and "alkynyl" as used herein whether on its own or as part of a larger group includes both straight and branched chain radicals. The terms also includes those radicals wherein one or more hydrogen atoms are replaced by fluorine.

The term "aryl" as used herein includes 5- to 10-membered substituted or unsubstituted aromatic rings or ring systems which may include bi-cyclic systems, including but not limited to phenyl and naphthyl, preferably phenyl.

The term "heteroaryl" as used herein includes 5- to 10-membered, substituted or unsubstituted, mono- or bicyclic aromatic rings containing up to three heteroatoms selected from oxygen, nitrogen and sulfur. A fused heteroaryl ring system may include carbocyclic rings and need include only one heterocyclic ring. Examples include benzofuran e.g. 2-benzofuran, benzothiophene e.g. 2-benzothiophene, benzoxazole e.g. 2-benzoxazole, benzothiazole e.g. 2-benzothiazole, benzopyran, quinoline, isoquinoline, pyridine, pyrimidine, pyrazine, oxadiazole, imidazole, tetrazole, furan, thiophene, oxazole and triazole.

The compounds of the invention preferably have a molecular weight of less than 800, more preferably less than 600.

Specific compounds of the invention that may be mentioned include those provided in the examples. A preferred list of specific compounds of the invention include:

2-[4-[5-[2-Chloro-4-[(2,4-dichlorophenylcarbonyl)amino]phenyl]furan-2-yl]-1,3-thiazol-2-yl]acetic acid, 2-[4-[5-[2-Chloro-4-[3-(4-bromo)phenylacryloylamino]phenyl]furan-2-yl]-1,3-thiazol-2-yl]acetic acid, 2-[4-[5-[2-Chloro-4-[3-(2,4-dichloro)phenylacryloylamino]phenyl]furan-2-yl]-1,3-thiazol-2-yl]acetic acid, 2-[4-[5-[2-Chloro-4-[3-(3,5-bistrifluoromethyl)phenylacryloylamino]phenyl]furan-2-yl]-1,3-thiazol-2-yl]acetic acid, 2-[4-[5-[2-Chloro-4-(3-phenylacryloylamino)phenyl]furan-2-yl]-1,3-thiazol-2-yl]acetic acid, 2-[4-[5-[2-Chloro-4-[(4-trifluoromethoxyphenylcarbonyl)amino]phenyl]furan-2-yl]-1,3-thiazol-2-yl]acetic acid, 2-[4-[5-[2-Chloro-4-[(benzothiophene-2-carbonyl)amino]phenyl]furan-2-yl]-1,3-thiazol-2-yl]acetic acid, 2-[4-[5-[2-Chloro-4-[(6-chloro-4H-chromene-3-carbonyl)amino]phenyl]furan-2-yl]-1,3-thiazol-2-yl]acetic acid, 2-[4-[5-[2-Chloro-4-[(3,4-dichlorophenylcarbonyl)amino]phenyl]furan-2-yl]-1,3-thiazol-2-yl]acetic acid, 2-[4-[5-[2-Chloro-4-[(3-methoxyphenylcarbonyl)amino]phenyl]furan-2-yl]-1,3-thiazol-2-yl]acetic acid, and 2-[4-[5-[2-Chloro-4-[(4-trifluoromethoxyphenylcarbonyl)amino]phenyl]furan-2-yl]-1,3-thiazol-2-yl]acetic acid, and pharmaceutically acceptable salts and prodrugs thereof.

Suitable pharmaceutically acceptable salts of the compounds of formula (I) include those derived from inorganic and organic bases. Examples of suitable inorganic bases include the hydroxides, carbonates, and bicarbonates of ammonia, lithium, sodium, calcium, potassium, aluminium, iron, magnesium, zinc and the like. Salts can also be formed with suitable organic bases. Such organic bases are well known in the art and may include amino acids such as arginine and lysine, mono-, di-, or trihydroxyalkylamines such as mono-, di-, and triethanolamine, choline, mono-, di-, and trialkylamines, such as methylamine, dimethylamine, and trimethylamine, guanidine; N-methylglucosamine; N-methylpiperazine; morpholine; ethylenediamine; N-benzylphenethylamine; tris(hydroxymethyl) aminomethane; meglumine; and the like.

Salts may be prepared in a conventional manner using methods well known in the art, for example by treatment of a solution of the compound of formula (I) with a solution of the base, for example, potassium or sodium hydroxide, or potassium or sodium hydrogen carbonate.

The invention also includes prodrugs of the aforementioned compounds. A prodrug is an inactive or protected derivative of an active ingredient or a drug, which is converted to the active ingredient or drug in the body. Examples of prodrugs include pharmaceutically acceptable esters, including $C_1$-$C_6$ alkyl esters and pharmaceutically acceptable amides, including secondary $C_1$-$C_3$ alkylamides.

Prodrugs may be prepared in a conventional manner using methods well known in the art, for example reaction of the free acid under conditions suitable for the formation of an ester or amide bond.

As described herein, for all aspects of the invention, reference to compounds of formula (I) encompasses the pharmaceutically acceptable salts and prodrugs, e.g. esters, thereof.

Some of the compounds of this invention may be crystallised or recrystallised from solvents such as aqueous and organic solvents. In such cases solvates may be formed. This invention includes within its scope stoichiometric solvates including hydrates as well as compounds containing variable amounts of water that may be produced by processes such as lyophilisation.

Certain of the compounds of formula (I) may exist in the form of optical isomers, e.g. diastereoisomers and mixtures of isomers in all ratios, e.g. racemic mixtures. The invention includes all such forms, in particular the pure isomeric forms. The different isomeric forms may be separated or resolved one from the other by conventional methods, or any given isomer may be obtained by conventional synthetic methods or by stereospecific or asymmetric syntheses. Where a compound contains an alkene moiety, the alkene can be presented as a cis or trans isomer or a mixture thereof. When an isomeric form of a compound of the invention is provided substantially free of other isomers, it will preferably contain less than 5% w/w, more preferably less than 2% w/w and especially less than 1% w/w of the other isomers.

Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably at least 10% of a compound of formula (I).

The compounds of formula (I) can be prepared by art-recognized procedures from known or commercially available starting materials. If the starting materials are unavailable from a commercial source, their synthesis is described herein, or they can be prepared by procedures known in the art.

The invention also provides a process for preparing a compound of formula (I), comprising:

treating a compound of formula (II):

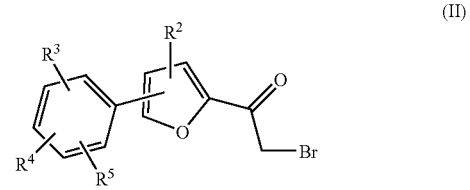

(II)

wherein $R^2$, $R^3$, $R^4$ and $R^5$ are as defined in formula (I), with a compound of formula (III):

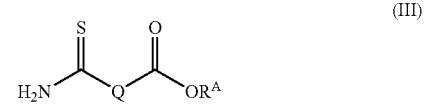

(III)

wherein Q is as defined in formula (I), $R^A$ is $C_{1-6}$ alkyl e.g. $CH_3$ or $C_2H_5$, or a protecting group e.g. $CH_2Ph$, for example by stirring in a suitable solvent e.g. isopropanol. Subsequently the $OR^A$ group is preferably deprotected to give the free carboxylic acid, wherein $R^A$ is hydrogen. Compounds of formula (III) may be commercially available. They and derivatives thereof may also be prepared by methods well known to those skilled in the art A compound of formula (II) may be prepared from a compound of formula (IV):

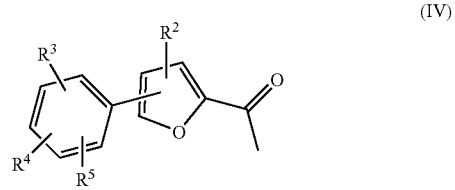

(IV)

wherein $R^2$, $R^3$, $R^4$ and $R^5$ are as defined in formula (I), by use of a suitable bromination reagent, e.g. tetrabutylammonium tribromide and acetic acid in dichloromethane.

A compound of formula (IV) may be prepared by a coupling reaction between a compound of formula (V), wherein $R^B$ is hydrogen, $C_{1-6}$ alkyl or $C_{3-6}$ cycloalkyl and $R^3$, $R^4$ and $R^5$ are as defined in formula (I), and a compound of formula (VI), wherein $R^C$ is hydrogen or bromine and $R^2$ is as defined in formula (I), using an appropriate catalyst, for example tetrakis(triphenylphosphine)palladium with a suitable base, for example sodium carbonate in a suitable solvent, for example 1,2-dimethoxyethane.

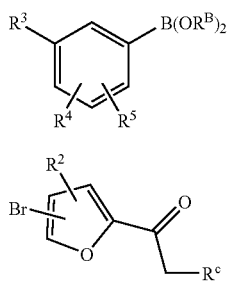

(V)

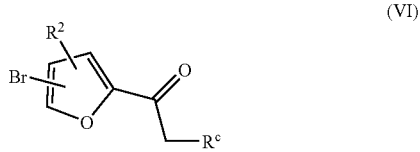

(VI)

Compounds of formula (V) as defined above may be commercially available. They and derivatives thereof may also be prepared by methods well known to those skilled in the art.

Compounds of formula (VI), wherein $R^C$ is hydrogen and $R^2$ is as defined in formula (I), may be prepared by conversion from a compound of formula (VII), wherein $R^D$ is hydrogen and $R^2$ is as defined in formula (I), by alkylation with for example a methyl Grignard reagent followed by oxidation with a suitable oxidation reagent, for example manganese dioxide.

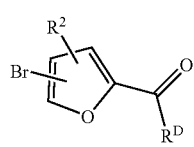

(VII)

Alternatively compounds of formula (VI), wherein $R^C$ is bromine and $R^2$ is as defined in formula (I), may be prepared by reaction of compounds of formula (VII), wherein $R^D$ is OH and $R^2$ is as defined in formula (I), with thionyl chloride followed by reaction with diazomethane or a suitable replacement reagent, e.g. TMSCHN$_2$ in a suitable solvent, e.g. THF followed by hydrobromination. The compounds of formula (VII) are commercially available.

In addition compounds of formula (I), wherein one or more of $R^3$, $R^4$ and $R^5$ is NHCOR$^8$, may be prepared by reaction of compounds of formula (VIII), wherein one or more of $R^3$, $R^4$ and $R^5$ is NH$_2$, $R^2$ and Q are as defined in formula (I) and $R^A$ is as defined in formula (III), with a compound of formula (IX), wherein $R^8$ is as defined in formula (I), in an amide bond formation reaction using either a suitable activation of the carboxylic acid, for example active ester formation and reaction using, for example DCC/HOBt, TBTU/HOAt or EDC/HOBt in a suitable solvent, e.g. THF, DCM or DMF; or by conversion to an acid chloride using, for example oxalyl chloride in THF/DMF followed by stirring of the acid chloride in a suitable solvent and base, for example pyridine. The example below has $R^3$ as NH$_2$ in the compound of formula (VIII):

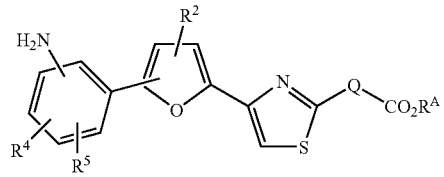

(VIII)

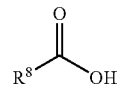

(IX)

Compounds of formula (IX), wherein $R^8$ is as defined in formula (I), may be commercially available.

Compounds of formula (VIII), wherein one or more of $R^3$, $R^4$ and $R^5$ is NH$_2$, $R^2$ and Q are as defined in formula (I) and $R^A$ is as defined in formula (III), may be prepared from other compounds of formula (X), wherein one or more of $R^3$, $R^4$ and $R^5$ is NO$_2$, $R^2$ and Q are as defined in formula (I) and $R^A$ is as defined in formula (III), by reduction using, for example H$_2$/Pd—C in a suitable solvent, e.g. EtOH, THF or by reduction with Zn dust in acetic acid/EtOH. The example below has $R^3$ as NO$_2$ in the compound of formula (X):

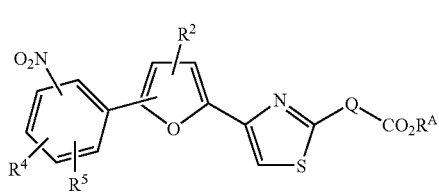

(X)

Compounds of formula (X) may be prepared by reaction of a compound of formula (XI), wherein $R^4$ and $R^5$ are as defined in formula (I), with a compound of formula (XII), wherein $R^2$ is as defined in formula (I), via conversion of the aniline to the diazonium compound using for example sodium nitrite in HCl and coupling to the furan using, for example copper (II) chloride.

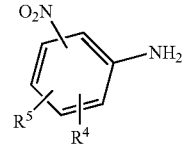

(XI)

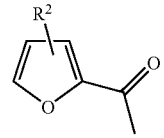

(XII)

Compounds of formula (XI) and (XII) may be commercially available. They and derivatives thereof may also be prepared by methods well known to those skilled in the art.

During the synthesis of the compounds of formula (I), labile functional groups in the intermediate compounds, e.g. hydroxy, carboxy and amino groups, may be protected. The protecting groups may be removed at any stage in the synthesis of the compounds of formula (I) or may be present on the final compound of formula (I). A comprehensive discussion of the ways in which various labile functional groups groups may be protected and methods for cleaving the resulting protected derivatives is given in for example *Protective Groups in Organic Chemistry*, T. W. Greene and P. G. M. Wuts, (Wiley-Interscience, New York, 2nd edition, 1991).

Further details for the preparation of compounds of formula (I) are found in the examples.

The compounds of formula (I) may be prepared singly or as compound libraries comprising at least 2, for example 5 to 1,000 compounds, and more preferably 10 to 100 compounds of formula (I). Libraries of compounds of formula (I) may be prepared by multiple parallel synthesis using either solution phase or solid phase chemistry, by procedures known to those skilled in the art.

Thus according to a further aspect of the invention there is provided a compound library comprising at least 2 compounds of formula (I) or pharmaceutically acceptable salts or prodrugs thereof.

Any novel intermediate compounds of formula (II) and formula (X) as described herein also fall within the scope of the present invention. Preferred intermediate compounds of the invention include the compounds of Example 1d), 1e), 2b), 2c), 3b), 3c), 4b), 4c) and the corresponding bromoketones of formula (II) and nitro-compounds of formula (X) used in the preparation of compounds given in Examples 5-24.

The invention also provides a compound of formula (I) when prepared by any of the above mentioned methods.

The invention also provides a compound of formula (I), without proviso i), for use in medicine.

The pharmaceutically effective compounds of formula (I) and pharmaceutically acceptable salts and prodrugs thereof, may be administered in conventional dosage forms prepared by combining a compound of formula (I) ("active ingredient") with standard pharmaceutical carriers or excipients according to conventional procedures well known in the art. These procedures may involve mixing, granulating and compressing or dissolving the ingredients as appropriate to the desired preparation.

According to a further aspect of the invention there is provided a pharmaceutical composition comprising a compound of formula (I), without proviso i), or a pharmaceutically acceptable salt or prodrug thereof, together with one or more pharmaceutically acceptable carriers or excipients.

The pharmaceutical compositions of the invention maybe formulated for administration by any route, and include those in a form adapted for oral, topical or parenteral administration to mammals including humans.

Pharmaceutical formulations may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318, (1986).

Pharmaceutical formulations adapted for topical administration may be formulated as ointments, creams, suspensions, lotions, powders, solutions, pastes, gels, impregnated dressings, sprays, aerosols or oils and may contain appropriate conventional additives such as preservatives, solvents to assist chug penetration and emollients in ointments and creams.

For applications to the eye or other external tissues, for example the mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administration to the eye include eye drops wherein the active ingredient is dissolved or suspended in a suitable carrier, especially an aqueous solvent.

Pharmaceutical formulations adapted for topical administration in the mouth include lozenges, pastilles and mouth washes.

Pharmaceutical formulations adapted for rectal administration may be presented as suppositories or enemas.

Pharmaceutical formulations adapted for nasal administration wherein the carrier is a solid include a coarse powder having a particle size for example in the range 20 to 500 microns. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists which may be generated by means of various types of metered dose pressurised aerosols, nebulizers or insufflators.

Pharmaceutical formulations adapted for vaginal administration may be presented as pessaries, tampons, creams, gels, pastes, foams or spray formulations.

Pharmaceutical formulations adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the formulations may also include other agents conventional in the art having regard to the type of formulation in question, for example those suitable for oral administration may include flavouring agents.

The pharmaceutical formulations according to the invention are preferably adapted for oral administration.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice.

Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing.

Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, preferably from 10-60% by weight, of the active material, depending on the method of administration.

Pharmaceutical formulations may be presented in unit dose forms containing a predetermined amount of active ingredient per dose. Such a unit may contain for example 100 mg/kg to 1 mg/kg depending on the condition being treated, the route of administration and the age, weight and condition of the patient. Preferred unit dosage formulations are those containing a daily dose or sub-dose, as herein above recited, or an appropriate fraction thereof, of the active ingredient.

It will be recognized by one of skill in the art that the optimal quantity and spacing of individual dosages of a formula (I) compound will be determined by the nature and extent of the condition being treated, the form, route and site of administration, and the particular mammal being treated, and that such optimums can be determined by conventional techniques. It will also be appreciated by one of skill in the art that the optimal course of treatment, i.e. the number of doses of the compound of formula (I) given per day for a defined number of days, can be ascertained by those skilled in the art using conventional course of treatment determination tests.

The compounds of the present invention are useful in that they are capable of inhibiting heparanase. Thus, the compounds can be used in the treatment of cancers, preferably the treatment of metastatic tumour cells. Examples of such types of cells include melanoma, lymphoma, leukaemia, fibrosarcoma, rhabdomyosarcoma and mastocytoma. Types of cancer include colorectal cancer, prostate cancer, small cell lung cancer and non-small cell lung cancer, breast cancer, pancreatic cancer, renal cancer, gastric cancer, bladder cancer and ovarian cancer.

The compounds of the present invention can also be used in combination with one or more additional treatments or therapeutic compounds for cancer. Examples of such treatments include, surgery and radiation therapy. Examples of therapeutic compounds include but are not limited to cisplatin, cyclophosphamide, methotrexate, 5-fluorouracil, paclitaxel, docetaxel, vincristine, vinblastine, vinorelbine, doxorubicin, tamoxifen, toremifene, megestrol acetate, anastrozole, goserelin, anti-HER2 monoclonal antibody, capecitabine and raloxifene hydrochloride.

The compounds of the present invention can also be used in the treatment of angiogenesis and angiogenesis dependent diseases which include angiogenesis associated with the growth of solid tumours and retinopathy.

The compounds of the present invention can also be used in combination with one or more additional treatments or therapeutic compounds for angiogenesis. Examples of such other therapeutic compounds include but are not limited to recombinant platelet-derived growth factor-BB (Regranex™).

The compounds of the present invention can also be used in the treatment of inflammatory conditions including but not limited to rheumatoid arthritis, inflammatory bowel disease, and wound healing.

The compounds of the present invention can also be used in the treatment of autoimmune diseases such as but not limited to multiple sclerosis.

The compounds of the present invention can also be used in the treatment of cardiovascular diseases such as but not limited to blood clotting conditions, for example thromboembolic disease, arterial thrombosis and restenosis.

By the term "treating" is meant either prophylactic or therapeutic therapy.

In additional aspects, therefore, the present invention provides:

(i) the use of a compound of formula (I), without proviso i), as an inhibitor of the enzyme heparanase.

(ii) the use of a compound of formula (I), without proviso i), in the manufacture of a medicament for the treatment of cancers, preferably the treatment of metastatic tumour cells. Examples of such types of cells include melanoma, lymphoma, leukaemia, fibrosarcoma, rhabdomyosarcoma and mastocytoma. Types of cancer include but are not limited to, colorectal cancer, prostate cancer, small cell lung cancer and non-small cell lung cancer, breast cancer, pancreatic cancer, renal cancer, gastric cancer, bladder cancer and ovarian cancer.

(iii) the use of a compound of formula (I), without proviso i), in the manufacture of a medicament for the treatment of angiogenesis and angiogenesis dependent diseases which include angiogenesis associated with the growth of solid tumours and retinopathy.

(iv) the use of a compound of formula (I), without proviso i), in the manufacture of a medicament for the treatment of inflammatory conditions such as but not limited to rheumatoid arthritis, inflammatory bowel disease, and wound healing.

(v) the use of a compound of formula (I), without proviso i), in the manufacture of a medicament for the treatment of autoimmune diseases such as but not limited to multiple sclerosis.

(vi) the use of a compound of formula (I), without proviso i), in the manufacture of a medicament for the treatment of cardiovascular diseases such as but not limited to blood clotting conditions, for example thromboembolic disease, arterial thrombosis and restenosis.

(vii) a method for the treatment of cancers, preferably the treatment of metastatic tumour cells which comprises the step of administering to a patient an effective amount of a compound of formula (I), without proviso i).

(viii) a method for the treatment of angiogenesis and angiogenesis dependent diseases, which include angiogenesis associated with the growth of solid tumours and retinopathy, which comprises the step of administering to a patient an effective amount of a compound of formula (I), without proviso i).

(ix) a method for the treatment of inflammatory diseases, such as but not limited to rheumatoid arthritis, inflammatory bowel disease, and wound healing which comprises the step of administering to a patient an effective amount of a compound of formula (I), without proviso i).

(x) a method for the treatment of autoimmune diseases, such as but not limited to multiple sclerosis, which comprises the step of administering to a patient an effective amount of a compound of formula (I), without proviso i).

(xi) a method for the treatment of cardiovascular diseases, such as but not limited to blood clotting conditions, for example thromboembolic disease, arterial thrombosis and restenosis which comprises the step of administering to a patient an effective amount of a compound of formula (I), without proviso i).

All publications, including, but not limited to, patents and patent applications cited in this specification, are herein incorporated by reference as if each individual publication were specifically and individually indicated to be incorporated by reference herein as though fully set forth.

The invention will now be described by reference to the following examples, which are merely illustrative and are not to be construed as a limitation of the scope of the present invention.

EXAMPLE 1

2-[4-[5-(2,3-Dichlorophenyl)furan-2-yl]-1,3-thiazol-2-yl]acetic acid a)

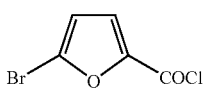

Thionyl chloride (18 ml, 246.8 mmol) was added to a solution/suspension of 5-bromo-2-furoic acid (10 g, 52.4 mmol) in benzene (100 ml) and the resulting mixture heated to 70° C. under reflux for 24 h. Solvents and excess thionyl chloride were then removed under reduced pressure to give the required compound as an off-white solid (10.41 g, 95%).

b)

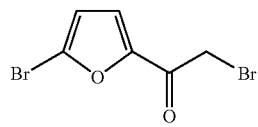

A solution of Example 1a) (5.3 g, 25 mmol) in dried dichloromethane (50 ml) was added dropwise to a stirred ice-cold solution of TMS diazomethane (2M in hexane; 25 ml, 50 mmol) in dry THF (50 ml) and the resulting mixture stirred at 0° C. for 2.5 h. A solution of HBr (48% aqueous solution; 25 ml) was then added and the mixture stirred for 30 min at 0° C., warmed to room temperature and diluted with ethyl acetate (300 ml). The organic mixture was washed with 0.5M NaOH, brine, dried (Na$_2$SO$_4$) and concentrated to give a pale yellow gum. The gum was crystallised by dissolving in 10 ml diethyl ether and slowly adding isohexane with ice-bath cooling to give an off-white solid (2.94 g). The mother liquors (total volume ~200 ml) were evaporated to give an orange solid which recrystallised from isohexane to give a second crop of the required compound (0.6 g). $^1$H NMR (CDCl$_3$) δ 4.30 (2H, s, CH$_2$), 6.57 (1H, d, ArH), 7.25 (1H, d, ArH).

c)

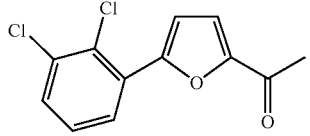

Example 1b) (536 mg, 2 mmol) and Pd(PPh$_3$)$_4$ (120 mg, 0.10 mmol) in DME (25 ml) were stirred at room temperature for 10 min. 2,3-Dichlorobenzene boronic acid (1.0 g, 5.24 mmol) was then added and the mixture heated to 80° C. for 3 h and for a further 18 h at room temperature. The reaction was diluted with water (50 ml) and ethyl acetate (100 ml), the aqueous layer separated and washed with ethyl acetate (50 ml×2). The combined organics were washed with brine, dried (MgSO$_4$) and evaporated to give the title compound as a dark orange gum. The product was purified by flash chromatography (10% EtOAc/isohexane) to give a pale yellow solid (315 mg, 62%). $^1$H NMR (CDCl$_3$) δ 2.56 (3H, s, CH$_3$), 7.27-7.33 (3H, m, ArH), 7.52 (1H, d, ArH), 7.90 (1H, d, ArH).

d)

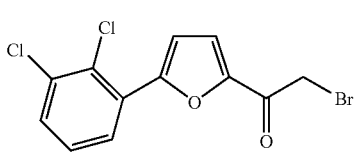

Example 1c) (240 mg, 0.941 mmol) was added in dichloromethane (9 ml) to tetrabutylammonium tribromide (458 mg, 0.95 mmol) followed by acetic acid (0.21 ml). After 18 h Na$_2$CO$_3$ (sat. solution; 7 ml) was added and the mixture stirred for 10 min. The aqueous layer was separated and washed with dichloromethane (2×10 ml) and the combined organic layers dried (MgSO$_4$) and evaporated under reduced pressure. The resultant product was purified by flash chromatography (1:1 DCM/isohexane) to give required product (159 mg, 50%). $^1$H NMR (CDCl$_3$) δ 4.40 (2H, s, CH$_2$), 7.35-7.39 (2H, m, ArH), 7.46 (1H, d, ArH), 7.54 (1H, d, ArH), 7.89 (1H, d, ArH).

e)

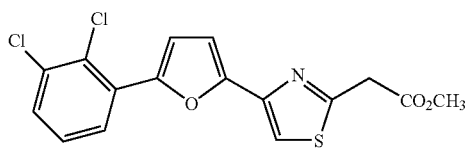

A mixture of Example 1d) (159 mg, 0.476 mmol) and methyl malonate monothioamide (69.6 mg, 0.52 mmol) in 2-propanol (9 ml) was stirred at room temperature for 48 h. Na$_2$CO$_3$ (20 ml) was then added and extracted with ethyl acetate (2×20 ml), the combined organic layers were washed with brine (10 ml), dried (MgSO$_4$) and evaporated. Column chromatography (1:1 DCM/isohexane) gave the required product (147 mg, 84%). $^1$H NMR (CDCl$_3$) δ 3.80 (3H, s, CH$_3$), 4.11 (2H, s, CH$_2$), 6.93 (1H, d, ArH), 7.25 (1H, dd, ArH), 7.40 (1H, d, ArH), 7.53 (1H, s, ArH), 7.85 (1H, d, ArH).

f)

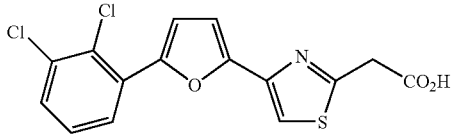

A solution of sodium hydroxide (3.96 g in 138 ml water) was prepared and 1.38 ml added to a solution of Example 1e) in MeOH (4.1 ml) and THF (0.9 ml), the mixture was stirred for 40 min at room temperature. The reaction mixture was neutralised (0.8 ml 1M HCl) and diluted with water (2 ml), partially evaporated and a further 1 ml water added to give a precipitate which was filtered, washed with water (2 ml) and dried to give 2-[4-[5-(2,3-dichlorophenyl)furan-2-yl]-1,3-thiazol-2-yl]acetic acid (31 mg). $^1$H NMR (DMSO) δ 3.95 (2H, s, CH$_2$), 6.92 (1H, d, ArH), 7.26 (1H, d, ArH), 7.35 (1H, t, ArH), 7.47 (1H, d, ArH), 7.71 (1H, s, ArH), 7.96 (1H, d, ArH). MS: 308 m/z (M-CO$_2$)$^-$.

EXAMPLE 2

2-[4-[5-[4-(2-Benzyloxyethylcarbamoyl)phenyl]furan-2-yl]-1,3-thiazol-2-yl]acetic acid a)

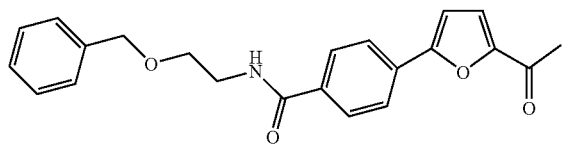

2-Bromo-5-acetylfuran (945 mg, 5.0 mmol) and Pd(PPh$_3$)$_4$ (290 mg, 0.25 mmol) were stirred in DME (50 ml) for 10 min at room temperature. Na$_2$CO$_3$ (2M, aq. solution; 20 ml) was then added and stirring continued for 10 min. 2-[4-(2-Benzyloxyethylcarbamoyl)]phenyl-1,2,3-dioxaborinane (3.39 g, 10 mmol) in DME (20 ml) was added and the mixture heated to 80° C. for 18 h. The mixture was cooled, diluted with ethyl acetate (100 ml) and water (100 ml) and the aqueous layer separated before washing with more ethyl acetate (3×50 ml). The combined organic layers were washed with brine, dried (MgSO$_4$) and evaporated to give a yellow gum. The product was purified by flash chromatography (5% EtOAc/hexane→100% EtOAc) to give the required product (1.8g). $^1$H NMR (CDCl$_3$) δ 2.57 (3H, s, CH$_3$), 3.70 (4H, s, 2×CH$_2$), 4.57 (2H, s, CH$_2$), 6.64 (1H, bs), 6.87 (1H, s), 7.28-7.41 (5H, m), 7.81-7.89 (4H, m).

b)

Example 2a) (1.8 g, 4 mmol) and tetrabutylammonium tribromide (2.25 g, 4.67 mmol) were dissolved in DCM (40 ml), acetic acid (1.1 ml) added and the solution stirred at room temperature for 18 h. The mixture was diluted with NaHCO$_3$ (sat. solution; 75 ml) and DCM (75 ml), the aqueous layer separated and further extracted with DCM (2×75 ml). The combined organic layers were washed with brine, dried (MgSO$_4$) and evaporated to give an orange gum, which was purified by flash chromatography to give the required product (600 mg).

c)

Example 2b) (600 mg, 1.36 mmol) and methymalonate monothioamide (181 mg, 1.36 mmol) were stirred in 2-propanol (40 ml) for 18 h. The resultant precipitate was filtered and the filtrate diluted with DCM and NaHCO$_3$ (sat. solution). The aqueous layer was separated and extracted with DCM, the combined organic extracts were dried (MgSO$_4$) and evaporated to give the solid product. The product was purified by prepHPLC to afford the required product (36 mg). $^1$H NMR (CDCl$_3$) δ 3.70 (4H, s, 2×CH$_2$), 3.80 (3H, s, CH$_3$), 4.10 (2H, s, CH$_2$), 4.58 (2H, s, CH$_2$), 6.63 (1H, bs), 6.85 (1H, d), 6.91 (1H, d), 7.29-7.42 (5H, m), 7.55 (1H, s), 7.75-7.83 (4H, m).

1 h. 2-Acetylfuran (15.94 g, 0.14 mol) and copper(II) chloride (3.41 g, 0.02 mmol) were added and the reaction was stirred at room temperature overnight. The reaction mixture was extracted with ethyl acetate (3×100 ml) and the combined organic fractions were washed with saturated aqueous sodium hydrogencarbonate solution, dried (Na$_2$SO$_4$) and concentrated. The resultant oil was purified by flash column chromatography (using 10% ethyl acetate/petroleum ether as eluent) to give the product as a yellow solid (22.54 g, 37%). $^1$H NMR (CDCl$_3$) δ 2.59 (3H, s), 7.34 (1H, d), 7.50 (1H, d), 8.21 (2H, m), 8.38 (1H, d).

d)

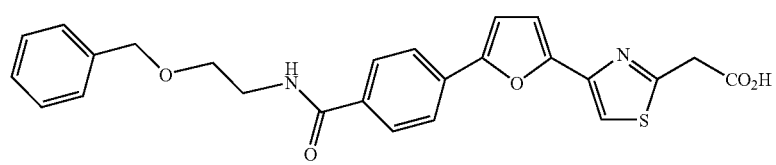

Example 2c) (34 mg, 0.071 mmol) was dissolved in a mixture of MeOH (3 ml) and THF (3 ml) and sodium hydroxide (15 mg in 1 ml water) added. The reaction was stirred at room temperature for 30 min, neutralised with HCl (1M) and concentrated until a precipitate formed. The precipitate was filtered, washed with water and dried under high vacuum to give 2-[4-[5-[4-(2-benzyloxyethylcarbamoyl)phenyl]furan-2-yl]-1,3-thiazol-2-yl]acetic acid (21 mg). $^1$H NMR (DMSO) δ 3.47-3.56 (4H, m, 2×CH$_2$), 4.15 (2H, s, CH$_2$), 4.51 (2H, s, CH$_2$), 6.92 (1H, d), 7.22-7.34 (6H, m), 7.88-8.01 (5H, m), 8.67 (1H, m). MS: 463 m/z (MH)$^+$.

EXAMPLE 3

2-[4-[5-[2-Chloro-4-[(2,4-dichlorophenylcarbonyl)amino]phenyl]furan-2-yl]-1,3-thiazol-2-yl]acetic acid a)

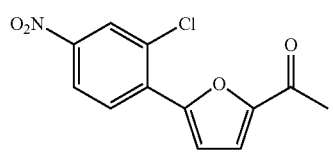

2-Chloro-4-nitroaniline (25 g, 0.14 mol) was suspended in water (50 ml) and concentrated hydrochloric acid (60 ml) and the mixture heated to 80° C. for 15 min. The mixture was cooled to 0° C. and a solution of sodium nitrite (11.04 g, 0.16 mol) in water (50 ml) was added dropwise. Once addition was complete, the reaction was stirred at 0° C. for b)

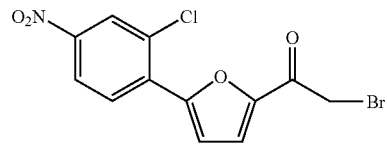

Tetrabutylammonium tribromide (32.79 g, 68.0 mmol) was added to a solution of Example 3a) (12.00 g, 45 mmol) in dichloromethane (250 ml) and acetic acid (1 ml). After stirring overnight at room temperature the reaction was washed with saturated aqueous sodium hydrogencarbonate solution dried (Na$_2$SO$_4$) and concentrated. The dark oil was purified by flash column chromatography (using 5% ethyl acetate/petroleum ether as eluent) to give the product as a yellow crystalline solid (7.24 g, 56%). $^1$H NMR (DMSO) δ 4.78 (2H, s), 7.64 (1H, d), 7.81 (1H, d), 8.25 (1H, d), 8.33 (dd, 1H), 8.45 (d, 1H).

c)

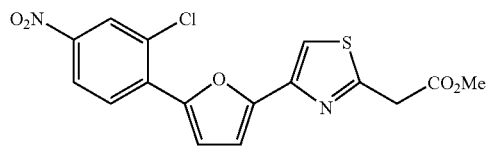

Methyl malonate monothioamide (3.33 g, 25 mmol) was added to a solution of Example 3b) (8.53 g, 25 mmol) in isopropanol (120 ml). After stirring overnight, the reaction was concentrated. The product was suspended in ethyl acetate (100 ml) and washed with saturated sodium hydrogencarbonate solution, dried (Na$_2$SO$_4$) and concentrated to give the product as an orange solid (6.56 g, 68%). $^1$H NMR (CDCl$_3$) δ 3.80 (3H, s), 4.15 (2H, s), 6.98 (d, 1H), 7.51 (d, 1H), 7.61 (s, 1H), 8.12 (d, 1H), 8.18 (dd, 1H), 8.33 (d, 1H).

d)

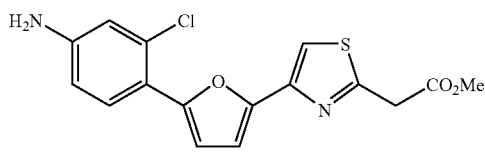

Zinc dust (6.67 g, 102 mmol) was added to a suspension of Example 3c) in ethanol/acetic acid (1:1, 150 ml). After 1 h, the reaction was concentrated and the residue stirred with dichloromethane (500 ml) and filtered through a bed of celite. The filtrate was washed sequentially with saturated sodium hydrogencarbonate solution (CARE: FOAMING) and brine, dried (Na$_2$SO$_4$) and concentrated to give the product as an orange solid (5.90 g, 99%). $^1$H NMR (CDCl$_3$) δ 3.78 (3H, s), 4.13 (2H, s), 6.63 (1H, dd), 6.75 (1H, d), 6.87 (1H, d), 6.97 (1H, d), 7.44 (1H, s), 7.69 (1H, d).

e)

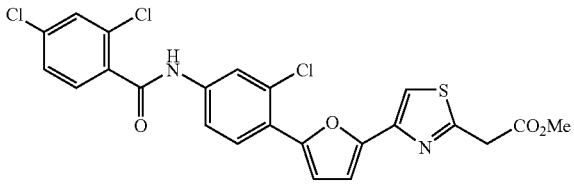

2,4-Dichlorobenzoyl chloride (3.55 ml, 25.3 mmol) was added to a solution of Example 3d) (5.90 g, 16.9 mmol) in pyridine (125 ml). After stirring for 4 h, the reaction was concentrated and the residue dissolved in dichloromethane (100 ml). This solution was extracted with 2M hydrochloric acid, washed with brine, dried (Na$_2$SO$_4$) and concentrated. The residue was triturated with ethyl acetate to give the product as an orange solid (6.45 g, 71%). $^1$H NMR (CDCl$_3$) δ 3.79 (3H, s), 4.14 (2H, s), 6.91 (1H, d), 7.19 (1H, d), 7.38 (1H, dd), 7.53 (3H, m), 7.75 (1H, d), 7.91 (2H, m), 8.02 (1H, s).

f)

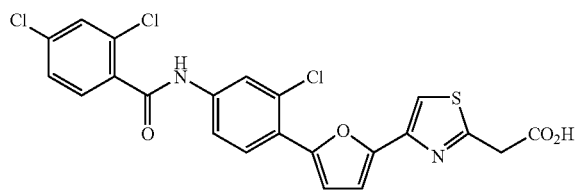

A solution of sodium hydroxide (2.40 g, 60 mmol) in water (30 ml) was added to a solution of Example 3e) (6.45 g, 12 mmol) in THF/MeOH (1:1, 90 ml) and the reaction was heated to 60° C. for 3 h. The reaction was cooled to room temperature and acidified with 2M hydrochloric acid. The resultant precipitate was collected by filtration to give the product as an orange solid (6.02 g, 99%). $^1$H NMR (DMSO) δ 4.14 (2H, s), 6.94 (1H, d), 7.20 (1H, d), 7.58 (1H, dd), 7.70 (2H, m), 7.79 (1H, d), 7.97 (1H, s), 8.03 (1H, d), 8.06 (1H, d), 10.87 (1H, s), 12.91 (1H, bs). MS (APCI) m/z: 460.8, 462.6 (M-CO$_2$).

EXAMPLE 4

2-[4-[5-[2-Chloro-4-[(4-trifluoromethoxyphenylcarbonyl)amino]phenyl]furan-2-yl]-1,3-thiazol-2-yl] acetic acid a)

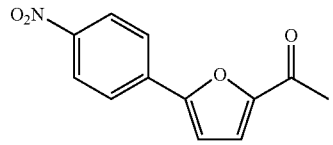

4-Nitroaniline (5 g, 36.20 mmol) was suspended in water (10 ml) and concentrated hydrochloric acid (15 ml) and the mixture heated to 80° C. for 15 min. The mixture was cooled to 0° C. and a solution of sodium nitrite (2.74 g, 39.82 mmol) in water (10 ml) was added dropwise. Once addition was complete, the reaction was stirred at 0° C. for 1 h. 2-Acetylfuran (4.77 g, 43.44 mmol) and copper(II)chloride dihydrate (0.80 g, 4.71 mmol) in water (4 ml) were added and the reaction was stirred at room temperature overnight. The reaction was partitioned with ethyl acetate (100 ml) and water (50 ml). The organic layer was removed and the aqueous layer was further extracted with ethyl acetate (2×100 ml). The organic fractions were combined and washed with saturated aqueous sodium hydrogencarbonate solution, dried (Na$_2$SO$_4$) and concentrated. The residue was triturated with ethyl acetate and petrol and collected by filtration to give the product as an orange/brown solid (2.87 g, 34%). $^1$H NMR (DMSO) δ 2.54 (3H, s), 7.54 (1H, d), 7.65 (1H, d), 8.14 (2H, d), 8.36 (2H, d).

b)

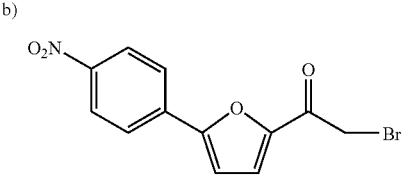

Tetrabutylammonium tribromide (6.58 g, 13.65 mmol) was added to a solution of Example 4a) (2.87 g, 12.41 mmol) in dichloromethane (50 ml) and acetic acid (0.5 ml). After stirring for 4 h at room temperature, the reaction was washed with saturated aqueous sodium hydrogencarbonate solution, dried (Na$_2$SO$_4$) and concentrated. The dark brown solid was purified by flash column chromatography (using dichloromethane/petrol 7:3 as eluent) to give the product as a bright yellow solid (1.75 g, 45%). $^1$H NMR (DMSO) δ 4.79 (2H, s), 7.61 (1H, d), 7.84 (1H, d), 8.18 (2H, dt), 8.40 (2H, dt).

c)

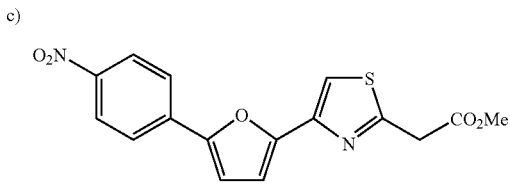

Methyl malonate monothioamide (0.90 g, 6.77 mmol) was added to a solution of Example 4b) (1.75 g, 5.64 mmol) in isopropanol (100 ml). After stirring overnight, the reaction was filtered and washed with isopropanol to yield the product as a bright yellow solid (1.83 g, 94%). $^1$H NMR (DMSO) δ 3.71 (3H, s), 4.32 (2H, s), 7.04 (1H, d), 7.47 (1H, d), 8.10 (2H, d), 8.13 (1H, s), 8.34 (2H, d).

d)

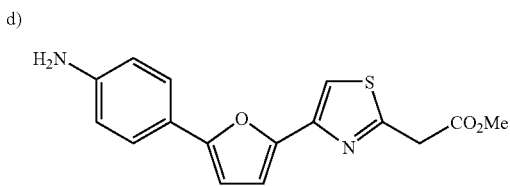

Zinc dust (3.42 g, 52.27 mmol) was added to a suspension of Example 4c) in ethanol/acetic acid (1:1, 150 ml). After 1 h, the reaction was concentrated and the residue partitioned with dichloromethane (200 ml) and saturated sodium hydrogencarbonate solution (200 ml) (CARE: FOAMING). The aqueous was further extracted with dichloromethane (2×100 ml). The organic extracts were combined, washed with brine, dried (Na$_2$SO$_4$) and concentrated to give the product as a brown foam/oil (1.56 g, 93%). $^1$H NMR (DMSO) δ 3.73 (3H, s), 4.28 (2H, s), 5.40 (2H, bs), 6.66 (2H, d), 6.69 (1H, d), 6.82 (1H, d), 7.51 (2H, d), 7.81 (1H, s).

e)

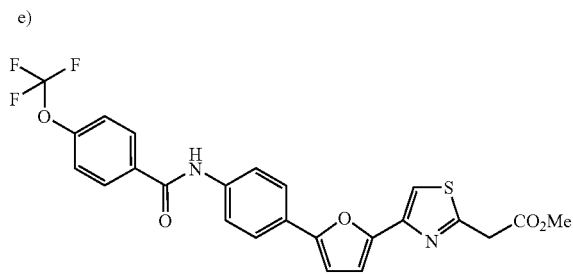

4-(Trifluoromethoxy)benzoyl chloride (75 µl, 0.48 mmol) was added to a solution of Example 4d) (100 mg, 0.32 mmol) in pyridine (3 ml). After stirring overnight, the reaction was concentrated and the residue dissolved in dichloromethane (10 ml). This solution was extracted with 2M hydrochloric acid, washed with brine, dried (Na$_2$SO$_4$) and concentrated. The residue was triturated with ethyl acetate/petrol and collected by filtration to give the product as a pale brown solid (80.1 mg, 47%). $^1$H NMR (DMSO) δ 3.74 (3H, s), 4.30 (2H, s), 6.92 (1H, d), 7.04 (1H, d), 7.58 (2H, d), 7.85 (2H, d), 7.92 (2H, d), 7.96 (1H, s), 8.14 (2H, d), 10.51 (1H, s).

f)

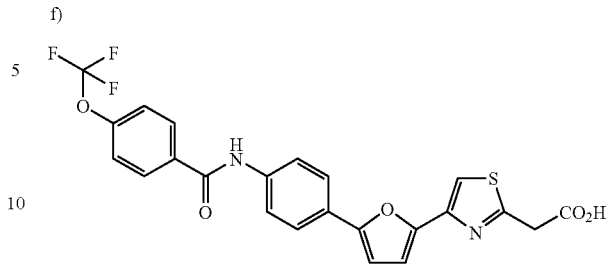

A solution of lithium hydroxide (11.9 mg, 0.50 mmol) in water (0.5 ml) was added to a solution of Example 4e) (50 mg, 0.10 mmol) in THF (1.5 ml) and the reaction was stirred overnight. The reaction mixture was acidified with 2M hydrochloric acid and the precipitate was collected by filtration to give the product as a brown solid (40.4 mg, 83%). $^1$H NMR (DMSO) δ 4.19 (2H, s), 6.93 (1H, d), 7.04 (1H, d), 7.59 (2H, d), 7.88 (5H, m), 8.15 (1H, d), 10.51 (1H, s), 12.94 (1H, bs). MS (APCI) m/z: 442.9, 445.1 (M-CO$_2$).

EXAMPLES 5-24

The following compounds were prepared according to the method of 4e) and 4f) using the appropriate acid chloride.

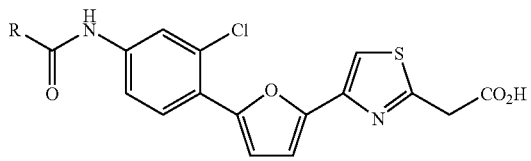

EXAMPLE 5

2-[4-[5-[2-Chloro-4-[3-(4-bromo)phenylacryloylamino]phenyl]furan-2-yl]-1,3-thiazol-2-yl]acetic acid

EXAMPLE 6

2-[4-[5-[2-Chloro-4-[3-(2,4-dichloro)phenylacryloylamino]phenyl]furan-2-yl]1,3-thiazol-2-yl]acetic acid

EXAMPLE 7

2-[4-[5-[2-Chloro-4-[3-(3,5-bistrifluoromethyl)phenylacryloylamino]phenyl]furan-2-yl]-1,3-thiazol-2-yl]acetic acid

EXAMPLE 8

2-[4-[5-[2-Chloro-4-(3-phenylacryloylamino)phenyl]furan-2-yl]-1,3-thiazol-2-yl]acetic acid

EXAMPLE 9

2-[4-[5-[2-Chloro-4-[(4-trifluoromethoxyphenylcarbonyl)amino]phenyl]furan-2-yl]-1,3-thiazol-2-yl]acetic acid

EXAMPLE 10

2-[4-[5-[2-Chloro-4-(2-methyl-3-phenylacryloylamino)phenyl]furan-2-yl]-1,3-thiazol-2-yl]acetic acid

EXAMPLE 11

2-[4-[5-[2-Chloro-4-[(benzothiophene-2-carbonyl)amino]phenyl]furan-2-yl]-1,3-thiazol-2-yl]acetic acid

EXAMPLE 12

2-[4-[5-[2-Chloro-4-[(6-chloro-4H-chromene-3-carbonyl)amino]phenyl]furan-2-yl]-1,3-thiazol-2-yl]acetic acid

EXAMPLE 13

2-[4-[5-[2-Chloro-4-[(4-chlorophenylcarbonyl)amino]phenyl]furan-2-yl]-1,3-thiazol-2-yl]acetic acid

EXAMPLE 14

2-[4-[5-[2-Chloro-4-[(4-bromophenylcarbonyl)amino]phenyl]furan-2-yl]-1,3-thiazol-2-yl]acetic acid

EXAMPLE 15

2-[4-[5-[2-Chloro-4-[(3,4-methylenedioxophenylcarbonyl)amino]phenyl]furan-2-yl]-1,3-thiazol-2-yl]acetic acid

EXAMPLE 16

2-[4-[5-[2-Chloro-4-[(3-chlorophenylcarbonyl)amino]phenyl]furan-2-yl]-1,3-thiazol-2-yl]acetic acid

EXAMPLE 17

2-[4-[5-[2-Chloro-4-[(5-bromopyrindine-3-carbonyl)amino]phenyl]furan-2-yl]-1,3-thiazol-2-yl]acetic acid

EXAMPLE 18

2-[4-[5-[2-Chloro-4-[(3,4-dichlorophenylcarbonyl)amino]phenyl]furan-2-yl]-1,3-thiazol-2-yl]acetic acid

EXAMPLE 19

2-[4-[5-[2-Chloro-4-[(3-trifluoromethyl-4-fluorophenylcarbonyl)amino]phenyl]furan-2-yl]-1,3-thiazol-2-yl]acetic acid

EXAMPLE 20

2-[4-[5-[2-Chloro-4-[(3-cyanophenylcarbonyl)amino]phenyl]furan-2-yl]-1,3-thiazol-2-yl]acetic acid

EXAMPLE 21

2-[4-[5-[2-Chloro-4-[(3-methoxyphenylcarbonyl)amino]phenyl]furan-2-yl]-1,3-thiazol-2-yl]acetic acid

EXAMPLE 22

2-[4-[5-[2-Chloro-4-[(4-trifluoromethoxyphenylcarbonyl)amino]phenyl]furan-2-yl]-1,3-thiazol-2-yl]acetic acid

EXAMPLE 23

2-[4-[5-[2-Chloro-4-[(furan-2-carbonyl)amino]phenyl]furan-2-yl]-1,3-thiazol-2-yl]acetic acid

EXAMPLE 24

2-[4-[5-[2-Chloro-4-[3-(4-methoxy)phenylacryloylamino]phenyl]furan-2-yl]-1,3-thiazol-2-yl]acetic acid

| Example | R | $^1$H NMR (DMSO) δ |
|---|---|---|
| 5 | 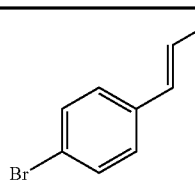 | 4.15(2H, s), 6.83(1H, d), 6.93(1H, d), 7.18(1H, d), 7.64 (6H, m), 7.95(1H, s), 8.00(1H, d), 8.09(1H, d), 10.55(1H, s), 12.89(1H, bs) |
| 6 | 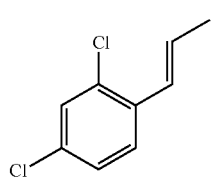 | 4.16(2H, s), 6.89(1H, d), 6.94(1H, d), 7.19(1H, d), 7.56 (1H, dd), 7.68(1H, dd), 7.77(1H, dd), 7.83(2H, m), 7.97 (1H, s), 8.01(1H, d), 8.10(1H, d), 10.66(1H, s), 12.91(1H, bs) |

-continued
| Example | R | ¹H NMR (DMSO) δ |
|---|---|---|
| 7 | 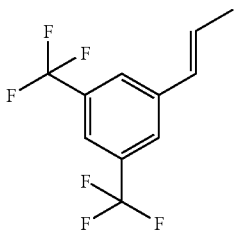 | 4.18(2H, s), 6.97(1H, d), 7.11(1H, d), 7.22(1H, d), 7.70 (1H, dd), 7.84(1H, d), 7.99(1H, s), 8.04(1H, d), 8.14(1H, d), 8.18(1H, bs), 8.39(2H, bs), 10.65(1H, s), 12.93(1H, bs) |
| 8 | 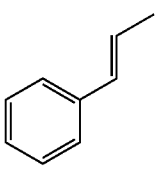 | 4.18(2H, s), 6.86(1H, d), 6.96(1H, d), 7.21(1H, d), 7.48 (3H, m), 7.68(4H, m), 7.99(1H, s), 8.03(1H, d), 8.13(1H, d), 10.58(1H, s) |
| 9 | 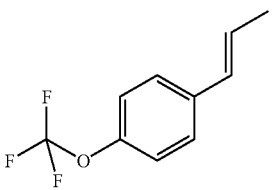 | 4.18(2H, s), 6.87(1H, d), 6.97(1H, d), 7.21(1H, d), 7.48 (2H, d), 7.70(2H, m), 7.82(2H, d), 7.99(1H, s), 8.03(1H, d), 8.13(1H, d), 10.63(1H, s), 12.93(1H, bs) |
| 10 | 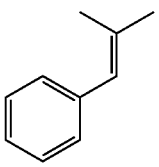 | 2.16(3H, d), 4.18(2H, s), 6.96(1H, d), 7.21(1H, d), 7.40 (2H, m), 7.49(4H, m), 7.83(1H, dd), 7.99(1H, s), 8.02(1H, d), 8.12(1H, d), 10.26(1H, s), 12.93(1H, bs) |
| 11 | 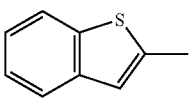 | 4.17(2H, s), 6.98(1H, d), 7.24(1H, d), 7.54(2H, m), 7.91 (1H, dd), 8.01(1H, s), 8.09(3H, m), 8.17(1H, d), 8.47(1H, s), 10.86(1H, s) |
| 12 | 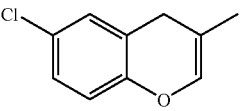 | 4.16(2H, s), 5.04(2H, s), 6.95(2H, m), 7.20(1H, d), 7.32 (1H, dd), 7.40(1H, d), 7.48(1H, s), 7.79(1H, dd), 7.99(1H, s), 8.03(1H, d), 8.06(1H, d), 10.41(1H, s), 12.92(1H, bs) |
| 13 | 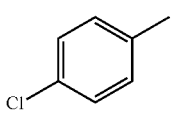 | 4.18(2H, s), 6.97(1H, d), 7.23(1H, d), 7.67(2H, d), 7.89 (1H, dd), 8.01(1H, s), 8.03(3H, m), 8.17(1H, d), 10.62(1H, s) |
| 14 | 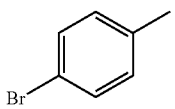 | 4.18(2H, s), 6.97(1H, d), 7.23(1H, d), 7.74(1H, d), 7.81 (1H, d), 7.81(1H, d), 7.88(1H, d), 7.95(1H, s), 7.99(2H, d), 8.06(1H, d), 8.17(1H, d), 10.62(1H, s), 12.96(1H, bs) |
| 15 | 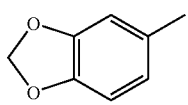 | 4.16(2H, s), 6.16(2H, s), 6.95(1H, d), 7.09(1H, d), 7.19(1H, d), 7.55(1H, d), 7.62(1H, dd), 7.86(1H, dd), 7.98(1H, s), 8.02(1H, d), 8.14(1H, d), 10.36(1H, s) |
| 16 | 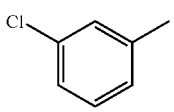 | 4.17(2H, s), 6.96(1H, d), 7.21(1H, d), 7.58(2H, m), 7.89 (3H, m), 7.98(1H, s), 8.04(1H, m), 8.15(1H, d), 10.62(1H, s), 12.93(1H, bs) |

-continued

| Example | R | ¹H NMR (DMSO) δ |
|---|---|---|
| 17 | 4-Br, 3-methyl pyridine | 4.16(2H, s), 6.97(1H, d), 7.25(1H, d), 7.86(1H, dd), 8.00 (1H, s), 8.07(1H, d), 8.14(1H, d), 8.61(1H, t), 8.96(1H, d), 9.11(1H, d), 10.80(1H, s) |
| 18 | 3,4-dichloro toluene | 4.17(2H, s), 6.97(1H, d), 7.23(1H, d), 7.87(2H, d), 7.97 (2H, d), 8.01(1H, s), 8.06(1H, d), 8.15(1H, d), 8.27(1H, d), 10.69(1H, s) |
| 19 | 4-fluoro-3-(trifluoromethyl)toluene | 4.18(2H, s), 6.97(1H, d), 7.24(1H, d), 7.69(1H, t), 7.87(1H, dd), 8.00(1H, s), 8.07(1H, d), 8.14(1H, d), 8.25(1H, dd), 8.32(1H, m), 10.75(1H, s) |
| 20 | 3-cyanotoluene | 4.16(2H, s), 6.95(1H, d), 7.22(1H, d), 7.79(1H, t), 7.87(1H, dd), 7.99(1H, s), 8.05(1H, d), 8.11(1H, d), 8.15(1H, d), 8.28 (1H, d), 8.45(1H, s), 10.71(1H, s) |
| 21 | 3-methoxytoluene | 3.87(3H, s), 4.17(2H, s), 6.96(1H, d), 7.21(3H, m), 7.89 (1H, dd), 7.99(1H, s), 8.04(1H, d), 8.16(1H, d), 10.51(1H, s) |
| 22 | 4-(trifluoromethoxy)toluene | 4.18(2H, s), 6.97(1H, d), 7.24(1H, d), 7.51(1H, d), 7.58 (2H, d), 7.87(1H, dd), 8.00(1H, s), 8.05(1H, d), 8.11(1H, d), 8.16(1H, d), 10.66(1H, s) |
| 23 | 2-methylfuran | 4.18(2H, s), 6.69(1H, d), 6.98(1H, d), 7.22(1H, d), 7.34 (1H, d), 7.78(4H, m), 8.04(2H, m) |
| 24 | 4-methoxytoluene | 3.87(3H, s), 4.20(2H, s), 6.73(1H, d), 6.98(1H, d), 7.08(2H, d), 7.22(1H, d), 7.62(1H, s), 7.65(2H, d), 7.72(1H, dd), 8.00 (1H, s), 8.03(1H, d), 8.14(1H, d), 10.50(1H, s), 12.95(1H, bs) |

Biological Data

The biological activity of the compounds of the invention may be tested in the following assay systems:

Heparanase assay: The assay is based upon the use of the specific binding of basic fibroblast growth factor (bFGF) to heparan sulphate. Heparan sulphate can be detected via binding of bFGF using a horse radish peroxidase-conjugated bFGF antibody. Following cleavage of high molecular weight heparan sulphate by heparanase, the smaller material generated will no longer adhere to the surface of a 96 well plate and hence heparanase activity can be followed as a reduction in bFGF binding.

Nunc Maxisorp 96-well plates are coated for 16 h at RT with 100 µl/well 0.04 mg/ml heparan sulphate in PBS. The wells are then aspirated and blocked for 1 h with 200 µl/well 1% BSA-PBS. Following five washes with 0.01% BSA, 0.05% Tween20 PBS (wash buffer), 100 µl of recombinant human basic FGF (90 ng/ml in 0.1% BSA/PBS) is added per well and the plate is incubated at room temperature for 1 h.

After a further five washes with the wash buffer, 10 µl of test compound (in 10% DMSO) and 90 µl of human heparanase in 100 mM Sodium acetate, 5 mM $CaCl_2$, pH 5.5 are added to each well and the plate incubated for 2 h at 37° C. The wells are washed again with wash buffer and 100 µl of bFGF antibody-horse radish peroxidase conjugate added. The plate is incubated at room temperature for 1 h and washed again five times with wash buffer. 100 µl of TMB peroxidase substrate is added and the colour allowed to develop for 10 min. The reaction is stopped with 50 µl 1M $H_2SO_4$ and the colour read at 450 nm on a plate reader.

Angiogenesis Assay: A commercial angiogenesis assay for analysing the angiogenic or anti-angiogenic properties of test compounds (AngioKit catalogue no. ZHA-1000, TCS CellWorks Ltd, Buckingham, U.K) was used. In this assay, human endothelial cells were co-cultured with other human cells in a specifically designed medium. The endothelial cells initially form small islands within the culture matrix. They subsequently proliferate and then enter a migratory phase during which they move through the matrix to form threadlike tubule structures. These gradually join up (by 12-14 days) to form networks of anatomising tubules which closely resemble a capillary bed structure. These tubules stain positive for von Willebrand's Factor, Platelet Endothelial Cell Adhesion Molecule-1 (PECAM-1 or CD31) and Intercellular Adhesion Molecule-2 (ICAM-2).

The assay is supplied as growing cultures at the earliest stage of tubule formation in a 24 well plate format. It is designed so that test compounds and conditioned media can be added to the cultures within individual wells. The resulting effect on tubule formation can then be monitored. Positive and negative test agents are provided in the kit, e.g. Vascular Endothelial Growth Factor (VEGF) and sumarin. All reagents were included as part of the kit and the assay was performed according to the protocol supplied by TCS CellWorks Ltd. Briefly, on day 1, fresh growth medium, medium plus control agent or medium plus test compound was added to the cells and the cultures were incubated at 37° C., 5% $CO_2$. Test compounds were dissolved in DMSO and the final concentration of DMSO in the medium did not exceed 0.1% (v/v). The specified medium was changed at days 4, 7 and 9 and the cells were monitored for growth. On day 11, the cells were washed with Dulbecco's Phosphate-Buffered Saline (PBS) and fixed using 70% ethanol (–20° C.) for 30 min at room temperature. After fixing, the cells were washed and treated with blocking buffer, 1% BSA in PBS. The cells were stained for PECAM-1 on the same day, following standard immunohistochemistry procedures well known to those skilled in the art, using mouse anti-human CD31 as the primary antibody and a goat anti-mouse IgG alkaline phosphate conjugate. Tubule formation was quantitatively assessed by measuring PECAM-1 positive staining using the image analysis program "Matrox inspector" to evaluate the percentage tubule staining relative to an untreated control.

The following table gives the heparanase and angiogenesis inhibitory activity of representative compounds of the invention.

| Example | Inhibition of Heparanase ($IC_{50}$, µM) | Angiogenesis ($IC_{50}$, µM) |
|---------|------------------------------------------|------------------------------|
| 4       | 3.5                                      | 0.2                          |
| 5       | 0.3                                      | 1.0                          |
| 6       | 0.3                                      | 0.5                          |
| 7       | 0.4                                      | 20                           |
| 8       | 0.5                                      | 15                           |
| 9       | 0.6                                      | 20                           |
| 11      | 0.4                                      | 20                           |
| 12      | 1.0                                      | —                            |
| 18      | 1.0                                      | 10                           |
| 21      | 7.0                                      | —                            |
| 22      | 1.0                                      | 0.5                          |

The invention claimed is:

1. A method for the therapeutic therapy of colorectal cancer, small cell lung cancer, non-small cell lung cancer, breast cancer, renal cancer, or gastric cancer, comprising administering to a patient suffering therefrom a pharmaceutically effective amount of a compound of formula I

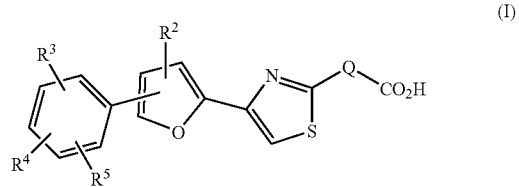

or a pharmaceutically acceptable salt or prodrug thereof:
wherein Q is $(CH_2)_m(CH(R^1))_n(CH_2)_p$;
n is 0 or 1;
m and p are, independently, 0, 1 or 2;
$R^1$ is hydrogen, $C_{1-6}$ alkyl, $C_{2-6}$ alkenyl or $C_{3-6}$ alkynyl;
$R^2$ is hydrogen, halogen, $C_{1-6}$ alkyl optionally substituted by hydroxy or $C_{1-6}$ alkoxy, or phenyl optionally substituted by one or more substituents selected from halogen, $C_{1-6}$ alkyl, $CF_3$, $OCF_3$, $OR^6$, CN and methylenedioxo;
$R^3$, $R^4$ and $R^5$ are, independently, hydrogen, halogen, $C_{1-6}$ alkyl optionally substituted by hydroxy or $C_{1-6}$ alkoxy, $CF_3$, $OR^6$, $COR^7$, $NHCOR^8$, $NHCONHR^8$, $NHSO_2R^8$, $CONHR^9$, CN, $SO_2R^8$ or $NR^{10}R^{11}$;
$R^6$ is hydrogen, $C_{2-6}$ alkenyl, $C_{3-6}$ alkynyl, $C_{1-6}$ alkyl optionally substituted by hydroxy or $C_{1-6}$ alkoxy, aryl or heteroaryl, wherein the aryl and heteroaryl groups are optionally substituted by one or more substituents selected from halogen, $CF_3$, $OCF_3$, CN, $C_{1-6}$ alkyl, $C_{1-6}$ alkoxy and methylenedioxo;
$R^7$ is $C_{1-6}$ alkyl, $OR^6$ or phenyl optionally substituted by one or more substituents selected from halogen, $CF_3$, $OCF_3$, CN, $C_{1-6}$ alkyl, $C_{1-6}$ alkoxy and $NHCOR^8$;
$R^8$ is $C_{1-6}$ alkyl, $C_{2-6}$ alkenyl, or $C_{1-6}$ alkoxy, any of which is optionally substituted by aryl or heteroaryl, wherein the aryl and heteroaryl groups are optionally substituted by one or more substituents selected from halogen, $CF_3$, $OCF_3$, $OR^6$, CN, $C_{1-6}$ alkyl, methylenedioxo and $NR^{10}R^{11}$; $C_{3-6}$ cycloalkyl, wherein the cycloalkyl ring optionally contains up to two heteroatoms selected from $NR^{12}$, S and O; or aryl or heteroaryl, wherein the aryl and heteroaryl groups are optionally substituted by one or more substituents selected from halogen, $CF_3$, $OCF_3$, $OR^6$, CN, $C_{1-6}$ alkyl, methylenedioxo and $NR^{10}R^{11}$;

$R^9$ is $C_{1-6}$ alkyl, $C_{1-6}$ alkylphenyl, or phenyl, wherein the alkyl groups are optionally interrupted by oxygen and wherein the phenyl groups are optionally substituted by one or more substituents selected from halogen, $C_{1-6}$ alkyl, $CF_3$, $OCF_3$, CN, $C_{1-6}$ alkoxy and methylenedioxo;

$R^{10}$ and $R^{11}$ are, independently, hydrogen or $C_{1-6}$ alkyl, or together with the nitrogen atom to which they are attached, form a 5- to 6-membered heterocyclic group which optionally contains an additional heteroatom selected from $NR^{12}$, O and S; and $R^{12}$ is hydrogen or $C_{1-6}$ alkyl.

* * * * *